US009779209B2

(12) United States Patent
Greer

(10) Patent No.: US 9,779,209 B2
(45) Date of Patent: Oct. 3, 2017

(54) APPLICATION TO WORKER COMMUNICATION INTERFACE

(75) Inventor: Richard S. Greer, Roswell, GA (US)

(73) Assignee: Cerner Innovation, Inc., Kansas City, KS (US)

( * ) Notice: Subject to any disclaimer, the term of this patent is extended or adjusted under 35 U.S.C. 154(b) by 1119 days.

(21) Appl. No.: 11/778,733

(22) Filed: Jul. 17, 2007

(65) Prior Publication Data

US 2008/0021709 A1    Jan. 24, 2008

Related U.S. Application Data

(60) Provisional application No. 60/820,120, filed on Jul. 24, 2006.

(51) Int. Cl.
*G06Q 10/00* (2012.01)
*G06F 19/00* (2011.01)

(52) U.S. Cl.
CPC .......... *G06F 19/327* (2013.01); *G06F 19/322* (2013.01)

(58) Field of Classification Search
CPC ...... G06Q 50/22; G06Q 50/24; G06F 19/327; G06F 19/322; G06F 19/3418; A61B 5/0002; G08B 21/02
USPC .......................................................... 705/2
See application file for complete search history.

(56) References Cited

U.S. PATENT DOCUMENTS

| | | |
|---|---|---|
| 5,617,471 A | 4/1997 | Rogers et al. |
| 5,673,308 A | 9/1997 | Akhavan |
| 5,802,477 A | 9/1998 | Mizokami et al. |
| 5,960,404 A * | 9/1999 | Chaar ............. G06F 9/5038 705/7.15 |
| 6,151,619 A | 11/2000 | Riddle |
| 6,233,325 B1 | 5/2001 | Frech et al. |
| 6,374,102 B1 | 4/2002 | Brachman et al. |
| 6,564,049 B1 | 5/2003 | Dailey |
| 6,581,035 B1 | 6/2003 | Madan et al. |
| 6,628,765 B1 | 9/2003 | Bangs et al. |

(Continued)

*Primary Examiner* — Reginald R Reyes
(74) *Attorney, Agent, or Firm* — Shook, Hardy & Bacon L.L.P.

(57) ABSTRACT

A substantially real-time voice, text, and messaging communications system employs application triggers for communications. A system provides communication between an executable application and a worker The system comprises at least one repository including, mapping information associating predetermined indicators conveyed by transaction messages with tasks performed by corresponding workers and communication routing information for use in establishing communication with the corresponding workers. A filter automatically accesses transaction messages processed by an executable application and uses the mapping information to identify a predetermined indicator in a received transaction message and a particular worker associated with the received transaction message. A communication interface generates voice message data representing a voice message for communication to the particular worker in response to identifying the predetermined indicator in the received transaction message and uses the routing information to wirelessly communicate the voice message data to a voice message reproduction device borne by the particular worker. The voice message conveys information concerning content of the received transaction message.

13 Claims, 2 Drawing Sheets

(56) References Cited

U.S. PATENT DOCUMENTS

| | | |
|---|---|---|
| 6,901,255 B2 | 5/2005 | Shostak |
| 7,184,527 B1 | 2/2007 | Lin et al. |
| 2002/0002609 A1 | 1/2002 | Chung et al. |
| 2003/0005464 A1* | 1/2003 | Gropper ................ G06F 19/321 |
| | | 725/115 |
| 2003/0023748 A1 | 1/2003 | Takemoto et al. |
| 2003/0200226 A1 | 10/2003 | Wells et al. |
| 2004/0198328 A1 | 10/2004 | Brandenberger |
| 2005/0130639 A1 | 6/2005 | Smith |
| 2005/0170863 A1 | 8/2005 | Shostak |
| 2005/0204030 A1 | 9/2005 | Koch et al. |
| 2006/0049936 A1 | 3/2006 | Collins, Jr. et al. |
| 2006/0167738 A1 | 7/2006 | Spear et al. |
| 2007/0004971 A1 | 1/2007 | Riley et al. |

\* cited by examiner

APPLICATION TO WORKER COMMUNICATION INTERFACE

This is a non-provisional application of provisional application Ser. No. 60/820,120 filed Jul. 24, 2006, by R. S. Greer.

FIELD OF THE INVENTION

This invention concerns a system providing communication between an executable application and a worker involving generating voice message data for communication to a worker in response to processing transaction messages.

BACKGROUND OF THE INVENTION

Known systems lack efficiency in their workflow processes in the use of computers for retrieving and managing information. A workflow process comprises a sequence of tasks or steps for performance by a device and or worker, for example. Known systems involve expenditure of valuable time by a user in getting to, and accessing a PC, logging in to an application, and retrieving information concerning a task to be performed in a particular workflow. Repeated trips by a worker to a PC to check on availability of information are typically required involving wasted time. A system according to invention principle addresses these deficiencies and related problems.

SUMMARY OF THE INVENTION

A Voice Application Integration Filter (VAIF) operates with an inter-computer data exchange system and programmatic mapping scheme to automatically communicate a variety of information to user worn wireless communication badge devices, without manual intervention, in response to embedded application triggers, for example. A system provides communication between an executable application and a worker The system comprises at least one repository including, mapping information associating predetermined indicators conveyed by transaction messages with tasks performed by corresponding workers and with communication routing information for use in establishing communication with the corresponding workers. A filter automatically accesses transaction messages processed by an executable application and uses the mapping information to identify a predetermined indicator in a received transaction message and a particular worker associated with the received transaction message. A communication interface generates voice message data representing a voice message for communication to the particular worker in response to identifying the predetermined indicator in the received transaction message and uses the routing information to wirelessly communicate the voice message data to a voice message reproduction device borne by the particular worker. The voice message conveys information concerning content of the received transaction message.

DETAILED DESCRIPTION OF THE INVENTION

Figure 1:
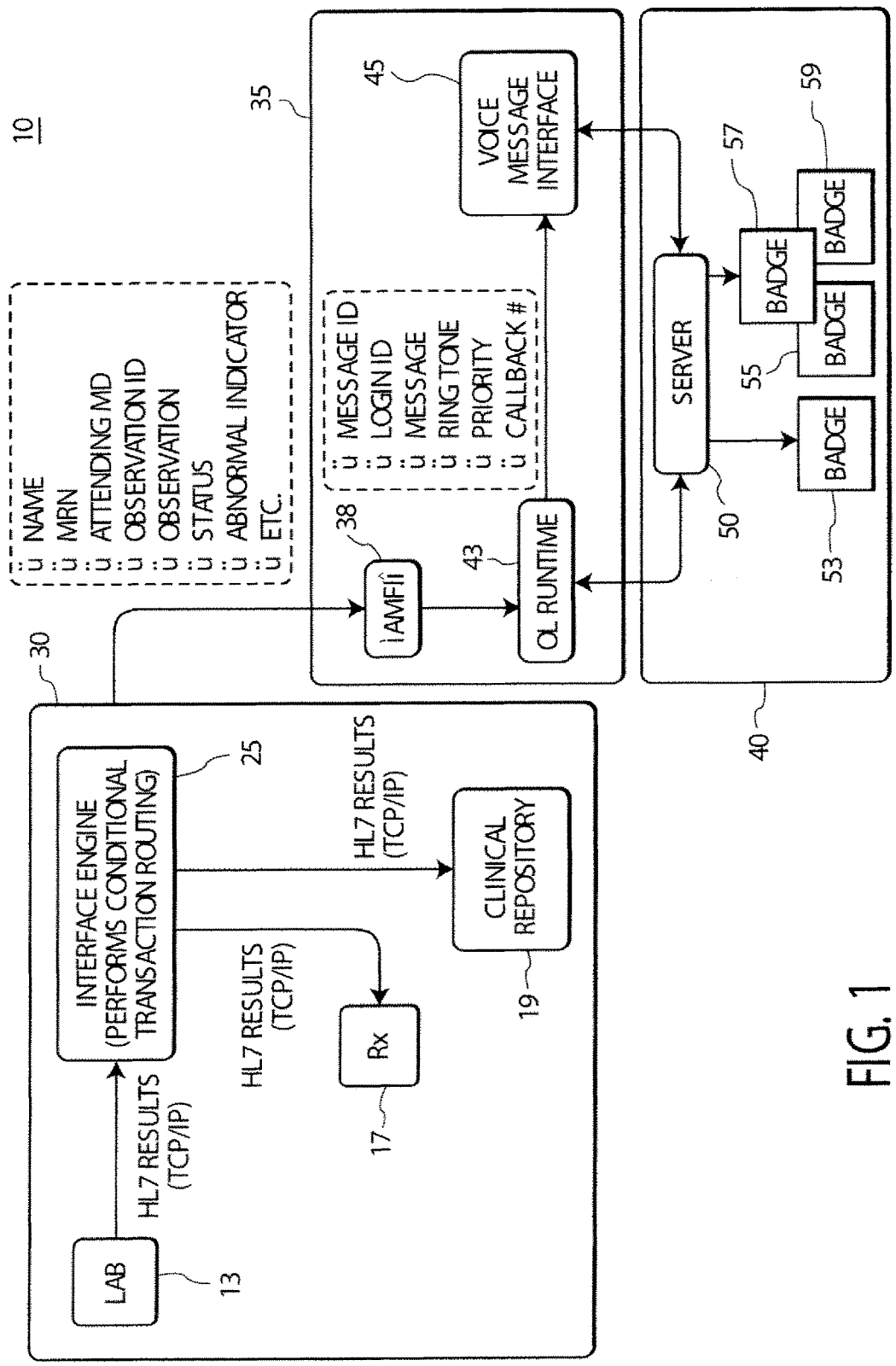
FIG. 1 shows a system providing communication between an executable application and a worker, according to invention principles.

A system provides substantially real-time voice, text and messaging communications for a mobile, geographically dispersed workforce within a large hospital facility or campus, for example, by employing trigger functions in executable applications. A Voice Application Integration Filter (VAIF) operates with an inter-computer data exchange system and programmatic mapping scheme to automatically communicate a variety of information to user worn wireless communication badge devices (such as devices compatible with those provided by Vocera) in response to embedded application triggers without manual intervention. The system communicates data identifying treatment orders and results information to clinicians and user-relevant information originating from other healthcare applications such as radiology, respiratory therapy, physical therapy, dietary, transport, housekeeping, and bed management, for example. The system streamlines workflow and improves worker and device productivity.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition.

A Workflow Management System is a software system that manages processes. It includes a process definition function that allows users to define a process that should be followed, an Event Monitor, which captures events from a Healthcare Information System and communicates the results to the Workflow Management System. A processor in the Management System tracks which processes are running, for which patients, and what step needs to be executed next, according to a process definition. The Management System includes a procedure for notifying clinicians of a task to be performed, through their worklists and a procedure for allocating and assigning tasks to specific users or specific teams. A document or record comprises a compilation of data in electronic form and is the equivalent of a paper document and may comprise a single, self-contained unit of information.

FIG. 1 shows system 10 providing communication between an executable application and a worker. System 10 employs multiple components including a communication system, Voice Messaging Interface (VMI) (e.g., available from Vocera and others), and a data exchange system for exchanging data between different computer systems using different data formats and communication protocols. System 10 includes a filter for capturing and parsing transaction messages such as messages compatible with the Health-Level7 (HL7) standard compatible format from a source application to extract and acquire data items. HL7 is a standard for the exchange, management and integration of data that supports clinical patient care, and the management and delivery of healthcare services by defining the protocol for exchanging clinical data between diverse healthcare information systems. The filter provides relevant data items for communication to a particular workflow, device, clinician or worker that needs to take action. The acquired data items are sent to a wireless communication badge device (e.g. such as one available from Vocera and others) after being translated from text to speech by the VMI. Pre-defined triggers associated with a particular workflow are employed by system 10 to provide a seamless and efficient workflow for healthcare workers, for example. Information relevant to worker specific tasks is sent automatically to the specific worker wireless communication badge device.

System 10 provides communication between an executable application and a worker using a clinical event interface 30 including a data exchange system 25. System 25 exchanges data between different computer systems (and associated executable applications) including voice messaging interface 35 and voice messaging system 40 using different data formats and communication protocols. Interface 30 also includes a workflow processor including a workflow engine for managing scheduling of performance of tasks by devices and personnel in a hospital, for example, by managing addition, deletion and amendment of tasks on worklists of devices and personnel. The workflow engine initiates performance of workflows in response to predetermined workflow process definitions stored in a repository in unit 30. The workflow engine uses voice messaging interface 35 and voice messaging system 40 to inform personnel of tasks for performance. Clinical event interface 30 includes at least one repository incorporating mapping information associating predetermined indicators conveyed by transaction messages with tasks performed by corresponding workers and communication routing information for use in establishing communication with the corresponding workers. Filter 38 automatically accesses transaction messages processed by an executable application and uses the mapping information to identify a predetermined indicator in a received transaction message and a particular worker associated with the received transaction message.

The transaction messages that are provided by laboratory information system 13 are communicated to pharmacy system 17 and clinical information repository system 19, and filter unit 38 via data exchange system 95. Transaction messages are also acquired from a variety of other systems (not shown to preserve drawing clarity) including a computerized order entry (CPOE) system, scheduling system, appointment system, treatment management system, admission, discharge and transfer (ADT) system and a clinical information processing system. The acquired transaction messages are communicated to destination systems via data exchange system 25. A communication interface in voice messaging system 40 generates voice message data representing a voice message for communication to the particular worker in response to identifying the predetermined indicator in the received transaction message. The communication interface uses the routing information to wirelessly communicate the voice message data to a voice message reproduction device borne by the particular worker. The voice message conveys information concerning content of the received transaction message.

In operation, an HL7 compatible transaction message (e.g., conveying laboratory test results) is communicated from laboratory information system 13 to data exchange system 25 using an IP/TCPIP compatible communication protocol in a hospital, for example. System 25 identifies an HL7 message based on predetermined indicators found in an HL7 message (or other format message) header or content. Data exchange system 25 routes the received transaction message to application message filter interface (AMFI) 38 as well as to pharmacy information system 17 and clinical information repository system 19. Data exchange system 25 replicates the transaction message data and sends the replicated transaction message data to a destination system and AMFI 38. The transaction message may, for example, comprise critical laboratory test results and contains data fields conveying, patient name and identifier, medical record number, attending physician identifier, test result (observation)

identifier, the observation result, status of the result (e.g., final, preliminary, first stage etc.), an abnormal indicator identifying an observation as abnormal and other items.

AMFI 38 parses the received transaction message and compares transaction message data elements with predetermined stored alert message generation criteria. The alert message generation criteria stored in a repository in voice messaging interface 35 associates particular HL7 message data elements with particular workflows and alert message destinations (e.g., workers). Specifically, the alert message generation criteria associates identifiers of workers with HL7 message data elements including, patient name and identifier, medical record number, attending physician identifier, test result (observation) identifier and other HL7 conveyed elements. The alert message generation criteria further associate identifiers of workers (such as physicians) with one or more particular workflows (and associated workflow identifiers) as well as one or more particular steps (and associated workflow step identifier) within a particular workflow.

AMFI 38 parses the received transaction message to identify HL7 message data elements and compares the HL7 message data elements with predetermined stored alert message generation criteria to identify a received transaction message that is associated with a particular physician or destination. Similarly, AMFI 38 may also identify a received transaction message that is associated with one or more other alert generation parameters including patient name and identifier, medical record number, attending physician identifier, test result (observation) identifier, workflow and step within a workflow. Thereby alert generation criteria act to initiate a request for an information alert message to be generated within a specific workflow, for example. In response to transaction message data matching alert message generation filter criteria, the transaction message is stored in a VMI database in VMI 45 for processing. The processing includes identifying a field in a transaction message, for example the attending MD field. In exemplary operation, messages that are received with an abnormal indicator flag set, along with the attending MD field, are sent to VMI 45 and from there to a wireless communication badge device that the attending MD is wearing, in response to an alert generation criteria match, for example.

Further in response to a determination a received transaction message is associated with one or more alert generation criteria and a particular workflow of a hospital, for example, a trigger is activated to convey a transaction message through AMFI 38 and to virtual message interface (VMI) 45 via online processor 43. Processor 43 communicates with VMI 45 via a VMI Application Programming Interface (API) and in response to matched alert generation criteria identified by AMFI 38 provides message generation data to VMI 45. The message generation data includes a destination identifier (e.g., a physician identifier), a message identifier, login id, the message, ring tone if applicable, a priority (e.g., stat, emergency) and a callback contact number, for example. Processor 43 provides the message which may comprise a predetermined message or a message derived by incorporation of transaction message data (e.g., test result values) and identifiers of workers (such as physicians) in a template message, for example. In system 10, if a transaction message meets alert generation criteria of AMFI 38, a second replicated transaction is created for transfer to a wireless communication badge device (e.g., devices 53-59). The second transaction is processed in parallel with the original HL7 transaction, which proceeds on to designated locations 17 and 19. If a transaction message does not meet alert generation criteria of AMFI 38, for examples because the transaction message does not relate to a customer-specified workflow for which an alert generation criteria trigger has been defined, the transaction message proceeds to its intended destination.

VMI 45 in voice messaging system 35, processes message generation data received from AMFI 38 to provide a transaction message in a format compatible with a Voice wireless communication application executing on server 50. VMI 45 communicates with server 50 using a TCP/IP protocol, for example. The server 50 communication application initiates communication of a text message to an appropriate corresponding wireless communication badge device of devices 53, 55, 57 and 59 using an Internet compatible communication protocol, for example. Processor 43 also bidirectionally communicates with server 50 and the communication application executing on server 50 to enable server 50 to acquire data supporting messaging and to enable processor 43 to query server 50 to obtain records of messages communicated and success or failure of the communications, for example. This communication may employ database querying protocols such as SQL, ODBC or an MS Access compatible query protocol, for example In operation of system 10, a respiratory therapist receives a next order in data received via a wireless communication badge device from the server 50 communication application while attending a patient at a hospital location. In contrast, a known system requires the respiratory therapist to walk back to a therapy department location and login to an associated computer application and retrieve the next order from the application. In another example, a clinician receives a message that laboratory test results are available for a particular patient while attending patients with a physician and substantially instantly communicates the results to the physician. Further, in a bed management process, house cleaning services are notified by a bed management application via system 10 when a room is vacant and ready to be cleaned. System 10 improves workflow operation by facilitating direct communication of healthcare applications with a healthcare worker using a process involving a hospital interface engine and AMFI 38 receiving an HL7 (for example) transaction message from a hospital application. In one embodiment the HL7 transaction message is matched against Hospital designated message workflows and if the filtered HL7 transaction message meets hospital alert message generation criteria, a corresponding HL7 transaction message is sent to VMI 45 which forwards a corresponding transaction message to a Voice wireless communication badge device (e.g., badge 53).

Figure 2:
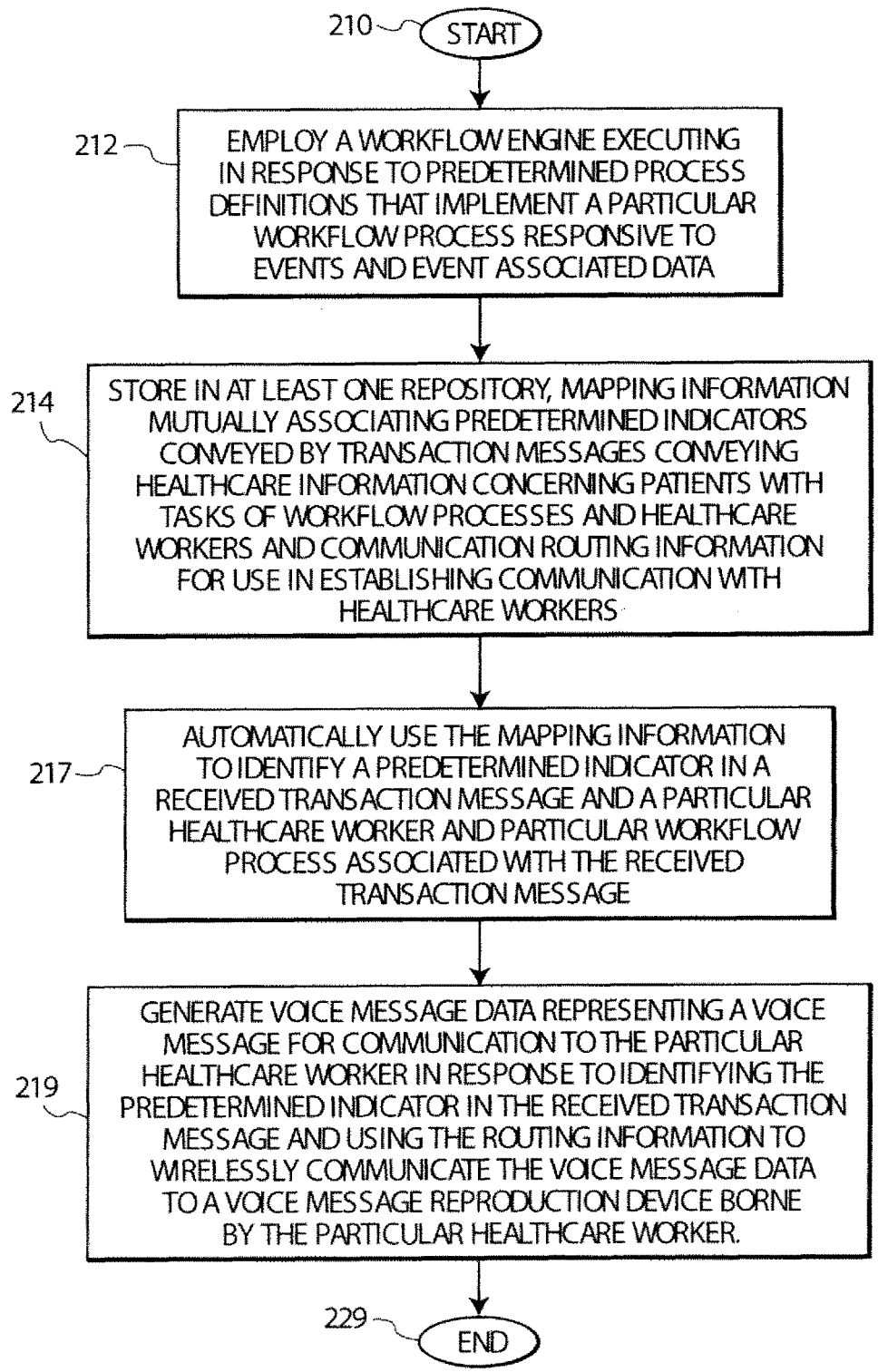
FIG. 2 shows a flowchart of a process performed by a system providing communication between an executable application and a worker, according to invention principles.

FIG. 2 shows a flowchart of a process performed by system 10 providing communication between an executable application and a worker. The steps of FIG. 2 may be performed automatically. In step 212 following the start at step 210, a workflow engine in interface 30 executes in response to predetermined process definitions that implement a particular workflow process responsive to events and event associated data. In another embodiment a task processor (instead of a workflow engine) in interface 30 manages a particular workflow process responsive to events and event associated data. Interface 30 in step 214 stores in at least one repository in unit 30 (or unit 35), mapping information mutually associating predetermined indicators conveyed by transaction messages conveying healthcare information concerning patients with tasks of workflow processes and with corresponding healthcare workers and with devices performing the tasks as well as with an individual task of a sequence of tasks of the particular workflow and with communication routing information for use in establishing communication between VMI 45 and corresponding healthcare workers and devices. The routing information includes healthcare worker specific communication information indicating one or more of (i) prioritized communication routes and (ii) a callback number. The transaction messages are HL7 (HealthLevel7) protocol compatible messages conveying healthcare information concerning patients.

In step 217 filter 38 automatically accesses transaction messages processed by an executable application in a healthcare organization. Filter 38 automatically, without human intervention, uses the mapping information to identify a predetermined indicator in a received transaction message and a particular healthcare worker and particular workflow process (including individual tasks of a particular workflow) associated with the received transaction message. The mapping information associates a predetermined indicator conveyed by the received transaction message with an individual task of a sequence of tasks of the particular workflow. The predetermined indicators comprise, a name, a Medical record Number (MRN), a Physician identifier or name, a patient identifier, an observation identifier, an encounter identifier, a medical observation, a patient status and an abnormal patient laboratory result or parameter indicator, for example. Filter 38 identifies fields in the received transaction message incorporating predetermined indicators identifying a physician and an abnormal test result indicator. Filter 38 comprises a conditional routing processor used in routing transaction messages to at least one of, (a) laboratory, (b) pharmacy and (c) a patient medical record in a healthcare organization.

In step 219 communication interface 35 generates voice message data representing a voice message for communication to the particular healthcare worker in response to identifying the predetermined indicator in the received transaction message. The generated voice message data includes a message together with at least one of, (a) a message identifier, (b) a login identifier and (c) a ring tone, for example. Communication interface 35 uses the routing information to wirelessly communicate the voice message data to a voice message reproduction device borne by the particular healthcare worker. The voice message conveys information concerning content of the received transaction message to inform a worker of the individual task of the particular workflow to be performed. Communication interface 35 generates voice message data representing a voice message containing an abnormal test result for communication to a particular healthcare worker, for example. The process of FIG. 2 terminates at step 229.

The system and process of FIGS. 1-2 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing, from the scope of the invention. System 10 is usable in any field employing applications for reporting messages to a user. For example, in Building Technology, an application sends a maintenance message to a worker from a check valve that needs to be serviced, or if an elevator breaks, an error message is sent directly to a service technician wearing a voice badge. On an assembly line when a stock part is in low supply system 10 notifies a user that stock is low. The processes and applications may in alternative embodiments, be located on one or more (e.g., distributed) processing devices accessing a network linking the elements of FIG. 1. Further, any of the functions and steps provided in FIGS. 1 and 2 may be implemented in hardware, software or a combination of both and may reside on one or more processing devices located at any location of a network linking the elements of FIG. 1 or another linked network including the Internet.

What is claimed is:

1. A system providing communication between an executable application and a worker, comprising:
   at least one repository including memory, the at least one repository comprising:
   mapping information indicating an association between predetermined indicators in transaction messages, the transaction messages encoding computerized physician order entry (CPOE) workflow tasks for performance by healthcare workers, wherein each transaction message includes, as generated by an executable application of the CPOE workflow of a medical clinical information system, at least one predetermined indicator encoded as a subcomponent within the transaction message, and
   communication routing information for use in establishing communication with said healthcare workers;
   an application message filter configured to, via a processor:
   automatically access the transaction messages provided by the executable application of the CPOE workflow of the medical clinical information system and being communicated from the executable application to a destination system, the transaction messages comprising patient specific clinical data, parse each of the transaction messages, and use the mapping information stored in the at least one repository to identify in each of the accessed and parsed transaction messages:
   at least one predetermined indicator subcomponent encoded in the transaction message,
   one of a plurality of CPOE workflows to which the transaction corresponds, and
   one particular healthcare worker for prioritized communication of the patient specific clinical data of the transaction message; and
   a communication interface comprising a voice message interface that is communicatively coupled to a voice wireless communication application executed via a server, the communication interface configured to:
   receive, from the application message filter, information including the at least one predetermined indicator subcomponent of a corresponding transaction message, the one CPOE workflow of the same corresponding transaction message, and the one particular healthcare worker;
   generate, in response to the receipt of the information from the application message filter, a voice message in a format usable by the voice wireless communication application executed via the server, the voice message for prioritized communication to the one particular healthcare worker identified and associated with the transaction message, wherein the voice message is generated by encoding a unique message identifier and audio content that includes at least a portion of the patient specific clinical data of the corresponding transaction message parsed by the application message filter that is relevant to the one CPOE workflow identified by the application message filter, and
   use the communication routing information stored in the repository to wirelessly communicate the voice message, via the voice wireless communication application executed via the server, to a voice message reproduction device of the one particular healthcare worker, wherein the voice message reproduction device facilitates audio playback of the voice message to the one particular healthcare worker.

2. The system according to claim 1, wherein said medical clinical information system further includes at least one of a laboratory information system and a pharmacy system, said application message filter automatically accesses said transaction messages and uses said mapping information to identify said predetermined indicator encoded as a subcomponent within the transaction messages without human intervention, and said predetermined indicators comprise at least one of, (a) a name, (b) a Medical record Number (MRN), (c) a Physician identifier or name, (d) a patient identifier.

3. The system according to claim 1, wherein said application message filter replicates said accessed transaction message and at least one of, sends the replicated transaction message to said destination system and uses said replicated transaction message as said accessed transaction message, said medical clinical information system includes at least one of, a scheduling system, an appointment system, a treatment management system, an admission, discharge and transfer (ADT) system and said predetermined indicators comprise at least one of, (a) an observation identifier, (b) an encounter identifier, (c) a medical observation, (d) a patient status and (e) an abnormal patient laboratory result or parameter indicator.

4. The system according to claim 3, wherein said mapping information associates said predetermined indicators encoded as subcomponents within the transaction messages with an individual CPOE workflow task of a sequence of CPOE workflow tasks of said particular CPOE workflow and the voice message generated by the communication interface informs a healthcare worker of said CPOE workflow individual task of said particular CPOE workflow to be performed and concurrently with communication of an accessed transaction message to said destination system.

5. The system according to claim 3, including a workflow engine executing in response to predetermined process definitions that implement said particular CPOE workflow responsive to events and event associated data.

6. A system providing communication between an executable application and a healthcare worker, comprising:

at least one repository including memory, the at least one repository comprising:

mapping information associating predetermined indicators encoded in transaction messages, the transaction messages encoding computerized physician order entry (CPOE) workflow tasks to be performed by corresponding healthcare workers, wherein each of the transaction messages includes, as generated by an executable application of the CPOE workflow of the medical clinical information system, at least one predetermined indicator encoded as a subcomponent within the transaction message, and communication routing information for use in establishing communication with said corresponding healthcare workers via a user-worn wireless voice message communication device; and an application message filter configured to, via a processor:

automatically access the transaction messages provided by the executable application of the CPOE workflow of the medical clinical information system and being communicated from the executable application to one or more of a laboratory information system, a pharmacy system, and a computerized order entry system, the transaction messages comprising patient specific clinical data, parse each of the transaction messages, use the mapping information stored in the repository to identify in each of the accessed and parsed transaction messages:

at least one predetermined indicator subcomponent encoded the transaction message, one of a plurality of CPOE workflows to which the transaction message corresponds, and a particular healthcare worker for prioritized communication of the patient specific clinical data of the transaction message; and a communication interface comprising a voice message interface that is communicatively coupled to a voice wireless communication application executed via a server, the communication interface, configured to:

receive, from the application message filter, information including the at least one predetermined indicator subcomponent of a corresponding transaction message, the one CPOE workflow of the same corresponding transaction message, and the one particular healthcare worker; generate, in response to receipt of the information from the application message filter, a voice message in a format usable by the voice wireless communication application executed via the server, the voice message for prioritized communication to the one particular healthcare worker identified and associated with the one transaction message, wherein the voice message is generated by encoding a unique message identifier and audio content that includes at least a portion of the patient specific clinical data of the corresponding transaction message parsed by the application message filter that is relevant to the one CPOE workflow identified by the application message filter, and use the communication routing information stored in the repository to wirelessly communicate the voice message, via the voice wireless communication application executed via the server, to a voice message reproduction device of the one particular healthcare worker, wherein the voice message communication device facilitates audio playback of the voice message to the one particular healthcare worker.

7. The system according to claim 6, wherein said application message filter comprises a conditional routing processor used in routing transaction messages in a healthcare organization.

8. The system according to claim 7, wherein said communication interface generates said voice message concurrently with communication of the one transaction message to the one or more of a laboratory information system, or a pharmacy system, and said conditional routing processor routes transaction messages to at least one of a (a) laboratory, (b) pharmacy, or (c) a patient medical record.

9. The system according to claim 6, wherein said routing information includes healthcare worker specific communication information indicating one or more of (i) prioritized wireless communication routes and (ii) a callback number and said communication interface communicates the voice message to the voice message communication device of the one particular healthcare worker along with at least one of, (a) a login identifier and (b) a ring tone.

10. A system providing communication between an executable application and a healthcare worker, comprising:
a task processor for managing a particular workflow process responsive to events and event associated data;
at least one repository including memory, the at least one repository comprising:
mapping information mutually associating predetermined indicators in transaction messages, the transaction messages encoding computerized physician order entry (CPOE) workflow tasks to be performed by healthcare workers, wherein each of the transaction messages includes, as generated by an executable application of the CPOE workflow of a medical clinical information system, at least one predetermined indicator encoded as a subcomponent within the transaction message, and
communication routing information for use in establishing communication with healthcare workers; an application message filter configured to, via a processor:
automatically access the transaction messages provided by the executable application of the CPOE workflow of the medical clinical information system and being communicated from the executable application to a destination system, the transaction messages comprising patient specific clinical data,
parse each of the transaction messages,
automatically use said mapping information stored in the at least one repository to identify, in each of the accessed and parsed transaction messages:
the at least one predetermined indicator subcomponent encoded in the transaction message, one of a plurality of CPOE workflows to which the transaction corresponds, and
one particular healthcare worker for prioritized communication of the patient specific clinical data of the transaction message; and
a communication interface comprising a voice message interface that is communicatively coupled to a voice wireless communication application executed via a server, the communication interface configured to:
receive, from the application message filter, information including the at least one predetermined indicator subcomponent of a corresponding transaction message, the one CPOE workflow of the same corresponding transaction message, and the one particular healthcare worker;
generate, in response to the receipt of the information from the application message filter, a voice message in a format usable by the voice wireless communication application executed via the server, the voice message for prioritized communication to the one particular healthcare worker identified and associated with the transaction message, wherein the voice message is generated by encoding a unique message identifier and audio content that includes at least a portion of the patient specific clinical data of the corresponding transaction message parsed by the application message filter that is relevant to the one CPOE workflow identified by the application message filter, and
use the communication routing information stored in the repository to wirelessly communicate the voice message, via the voice wireless communication application executed via the server, to a voice message reproduction device of the one particular healthcare worker, wherein the voice message is concurrently communicated to the destination, and wherein the voice message reproduction device facilitates audio playback of the voice message to the one particular healthcare worker.

11. A system providing communication between an executable application and a healthcare worker, comprising:
a workflow engine executing in response to predetermined process definitions that implement a particular workflow process responsive to events and event associated data;
at least one repository including memory, the at least one repository including:
mapping information mutually associating predetermined indicators in transaction messages, the transaction messages encoding computerized physician order entry (CPOE) workflow tasks of workflow processes to be performed by healthcare workers, wherein each of the transaction messages includes, as generated by an executable application of a CPOE workflow of the medical clinical information system, at least one predetermined indicator encoded as a subcomponent within the transaction message, and
communication routing information for use in establishing communication with healthcare workers; an application message filter configured to, via a processor:
automatically access the transaction messages provided by the executable application of the CPOE workflow of the medical clinical information system and being communicated from the executable application to a destination system, the transaction messages comprising patient specific clinical data,
parse each of the transaction messages, and
automatically use said mapping information to identify in each of the accessed and parsed transaction messages:
the at least one predetermined indicator encoded in the transaction message,
one particular healthcare worker for prioritized communication of the patient specific clinical data of the transaction message, and
one particular CPOE workflow to which the transaction message corresponds, based on the at least one predetermined indicator; and
a communication interface comprising a voice message interface communicatively that is coupled to a voice wireless communication application executed via a server, the communication interface configured to:
receive, from the application message filter, information including the at least one predetermined indicator subcomponent of a corresponding transaction message, the one CPOE workflow of the same corresponding transaction message, and the one particular healthcare worker;
generate, in response to the receipt of the information from the application message filter, a voice message in a format usable by the voice wireless communication application executed via the server, the voice message for prioritized communication to the one particular healthcare worker identified and associated with the transaction message,
wherein the voice message is generated by encoding a unique message identifier and audio content that includes at least a portion of the patient specific clinical data of the corresponding transaction message parsed by the application message filter that is relevant to the one CPOE workflow identified by the application message filter, and
use the communication routing information stored in the repository to wirelessly communicate the voice message, via the voice wireless communication application executed via the server, to a voice message reproduction device of the particular healthcare worker, wherein the voice message reproduction device facilitates audio playback of the voice message to the one particular healthcare worker.

12. The system according to claim 11, wherein said mapping information associates the at least one predetermined indicator encoded in the transaction message with one individual task of the CPOE workflow, and said voice message informs the one particular healthcare worker of said one individual task of said particular CPOE workflow to be performed.

13. The system according to claim 11, wherein said application message filter identifies fields in said transaction message incorporating predetermined indicators that identify a physician and an abnormal test result indicator, and said communication interface generates the voice message containing said abnormal test result for prioritized communication to said one particular healthcare worker.

* * * * *

UNITED STATES PATENT AND TRADEMARK OFFICE
CERTIFICATE OF CORRECTION

| | |
|---|---|
| PATENT NO. | : 9,779,209 B2 |
| APPLICATION NO. | : 11/778733 |
| DATED | : October 3, 2017 |
| INVENTOR(S) | : Richard S. Greer |

It is certified that error appears in the above-identified patent and that said Letters Patent is hereby corrected as shown below:

On the Title Page

Item (57) in the Abstract:
Line 4: "worker The" should read --worker. The--

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*